United States Patent [19]

Boesch et al.

[11] Patent Number: 5,143,126
[45] Date of Patent: Sep. 1, 1992

[54] VIBRATORY PROCESS AND APPARATUS FOR AGGLOMERATING AND METERING NON-FLOWABLE POWDERS

[75] Inventors: Beate Boesch, Roggenhouse, France; Satish C. Khanna, Bottmingen, Switzerland

[73] Assignee: Ciba-Geigy Corporation, Ardsley, N.Y.

[21] Appl. No.: 645,079

[22] Filed: Jan. 23, 1991

[30] Foreign Application Priority Data

Jan. 29, 1990 [CH] Switzerland .................. 266/90

[51] Int. Cl.⁵ .................. G01F 11/00; B65B 1/34
[52] U.S. Cl. .................. 141/1; 141/83; 141/11; 198/757; 222/361
[58] Field of Search .................. 141/1, 9, 11, 69; 209/920; 222/196, 405, 226, 233-235, 361, 362; 198/757, 392; 221/200, 168, 167

[56] References Cited

U.S. PATENT DOCUMENTS

| | | | |
|---|---|---|---|
| 392,911 | 11/1888 | Dean | 222/361 |
| 2,369,251 | 2/1945 | Reynolds | 222/361 |
| 3,135,429 | 6/1964 | Anderson | 222/361 |
| 3,209,900 | 10/1965 | Prutton | 198/757 |
| 3,788,449 | 1/1974 | Baberowski | 198/757 |
| 3,838,770 | 10/1974 | Caffa | 198/757 |
| 4,635,829 | 1/1987 | Brittingham, Jr. | 222/361 X |
| 4,688,610 | 8/1987 | Campbell | 141/83 |
| 4,709,837 | 12/1987 | Erdman | |
| 4,733,803 | 3/1988 | Sisson et al. | 222/361 X |
| 4,821,782 | 4/1989 | Ayer | 141/83 |

FOREIGN PATENT DOCUMENTS 3332528 3/1985 Fed. Rep. of Germany .
2140180 1/1973 France .

OTHER PUBLICATIONS

996 Die Pharmazie, vol. 35 (1980).

Primary Examiner—Ernest G. Cusick
Attorney, Agent, or Firm—JoAnn Villamizar; Harry Falber

[57] ABSTRACT

A vibratory conveyor for forming flowable grain agglomerations from previously poorly flowable fine-grained powder and thereafter conveying said agglomerations to a metering chamber which comprises a mechanical vibration device to agglomerate the poorly flowable powder, transport means for conveying the agglomerated powder and metering means for collecting and measuring the conveyed powder; and a method directed thereto wherein the poorly flowable powder is subjected to a mechanical vibration step prior to transport and metering.

6 Claims, 2 Drawing Sheets

VIBRATORY PROCESS AND APPARATUS FOR AGGLOMERATING AND METERING NON-FLOWABLE POWDERS

BACKGROUND OF THE INVENTION

The invention relates to a method of metering very small quantities of a non-flowable or poorly flowable powder, and to a corresponding apparatus therefor.

Many fine-grained powders are distinguished inter alia by the fact that they are either poorly flowable or completely non-flowable, but in any case they flow irregularly. Owing to the poor or very irregular flow of the powder, considerable difficulties arise in the accurate metering especially of very small quantities of such a powder. When the powder is introduced into a metering container or into a metering chamber, it often flows into the metering chamber only in surges, because the grains of powder adhere either to one another or to the surface of a feed device. Filling funnels for introducing the powder into the metering chamber therefore easily become blocked. This means that when the metering chamber is emptied at regular intervals, the quantity of powder located therein may vary very considerably. As long as the amount of powder supplied is very small owing to adhesion, the amount of powder passing into the metering chamber during the time in which the metering chamber is to be filled will also be only small. On the other hand, when there is a surge in the powder fed to the meeting container, i.e. when the blockage in a blocked filling funnel frees itself, the metering container will overflow, so that a suitable overflow container has to be provided. In the case of metering methods in which it is especially important that the quantity of powder metered should always be constant, or in which only very slight fluctuations in the relative weights of the metered quantities of powder are permissible, for example in the metering of pharmaceutical powders, the poor flow properties of the powder are especially disadvantageous since, in view of the subsequent administration of the metered quantity of powder, it is essential that the same quantity of powder should always be discharged from the metering chamber. This means that level indicators may be required for the metering chamber in order to ensure that the same quantity of powder is always discharged from the metering chamber, and this involves not inconsiderable expenditure.

One possible method by which poorly flowable or non-flowable powder can be rendered flowable, and hence metering can be simplified, consists in adding a so-called "lubricant" to the powder. Owing to adhesion forces between the surface of the fine powder grains and the surface of the lubricant, such lubricants form flowable powder/lubricant conglomerations. However, this method is disadvantageous in two respects. Firstly, for example in the case of so-prepared therapeutic agents for the treatment of human lungs, in many cases the lubricants cannot be dispersed by the "one-way system" lung; secondly, the conglomerations so formed are too coarse to permit sufficiently accurate metering of very small quantities. An example of such a lubricant that cannot be dispersed by the lungs is stearic acid (solid phase). When liquid lubricants are used to form the conglomerations, there do exist drying processes which can be used to remove the lubricants from the conglomerations again after conglomeration formation, but, depending on the drying process used, either the dried conglomerations then immediately disintegrate again into non-flowable fine powder, or the conglomerations are very hard; in the former case, the drying process results in the same problem of transporting poorly flowable fine powder grains, and in the latter case it is not possible to comminute the conglomerations although, in view of the intended method of administration (e.g. powder inhalation), comminution is essential because the conglomerations are too coarse in the uncomminuted state. Furthermore, it has also been found that when liquid lubricants are added, the size of the crystals of the individual fine powder grains changes so that, even if it were possible to comminute the conglomerations after drying, the powder grains would still be too coarse for inhalation.

BRIEF DESCRIPTION OF THE DRAWING

The invention is described in greater detail below with reference to the drawing, in which.

Figure 1:
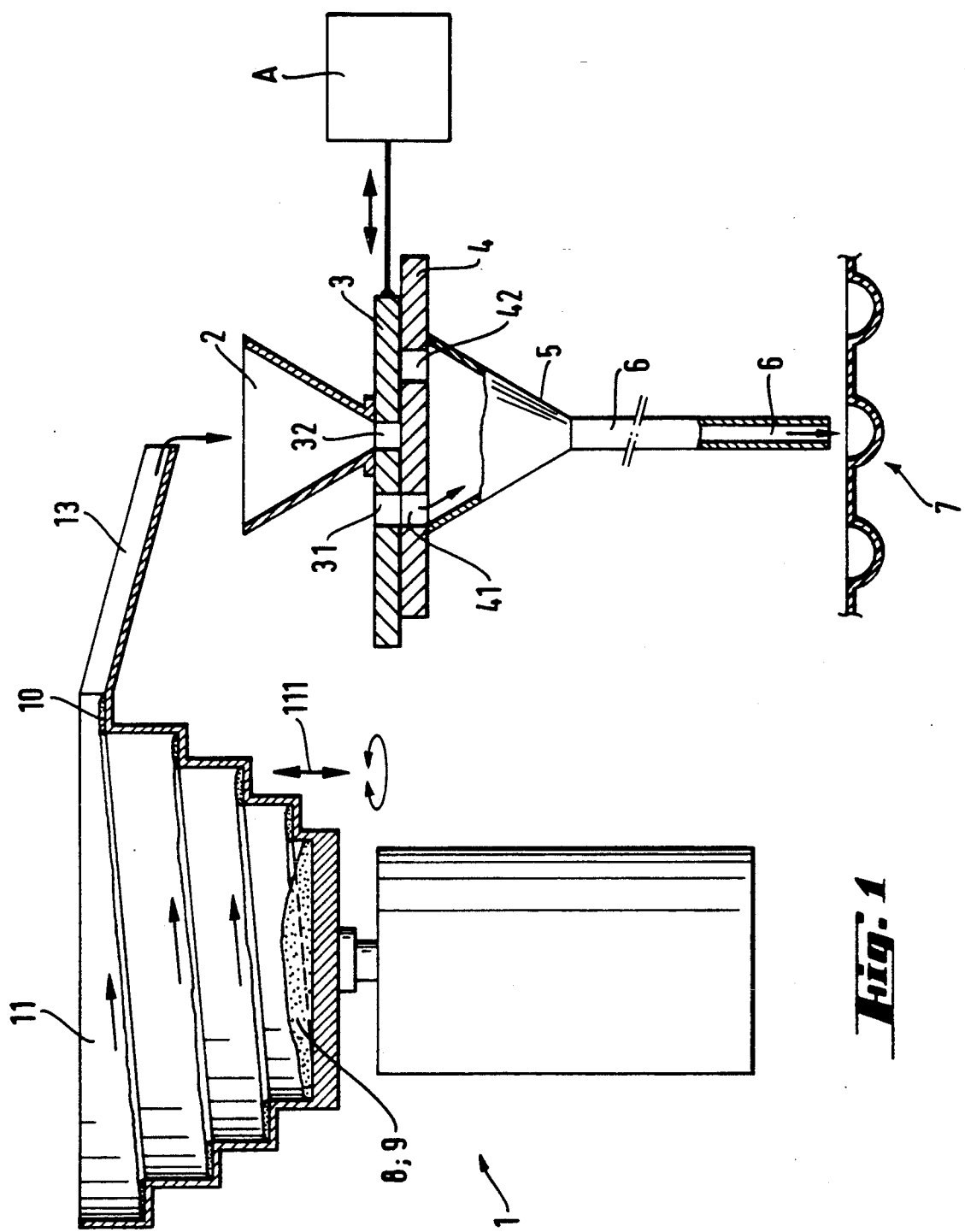
FIG. 1 is a general schematic view of the apparatus for carrying out the method according to the invention, partly in axial section.

The apparatus shown in FIG. 1 comprises a vibratory conveyor 1, a first filling funnel 2, metering means in the form of a movable first plate 3 having two openings 31 and 32 and a fixed second plate 4 having two openings 41 and 42, a second filling funnel 5 and a pipe 6.

Figure 2C:
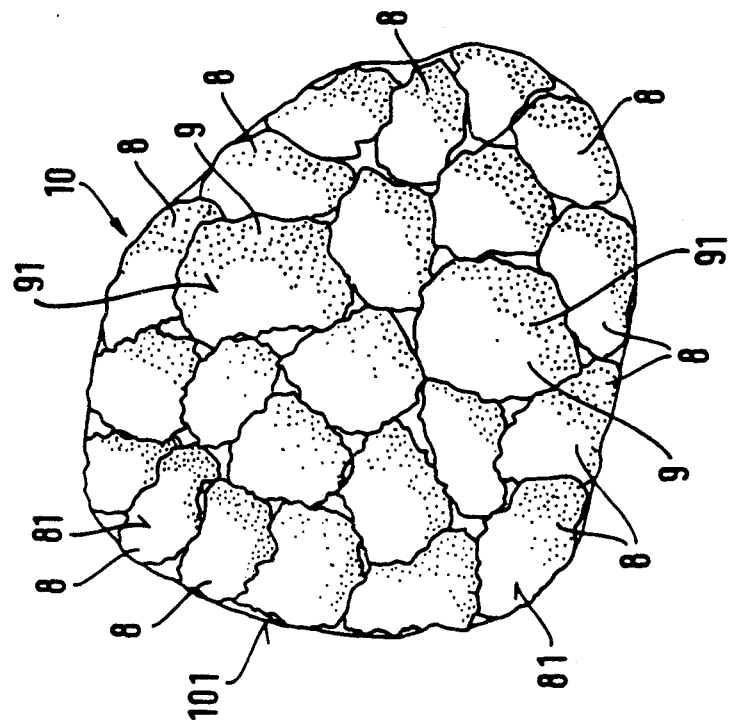
FIG. 2a–c is a view of the non-flowable or poorly flowable powder grains and of the flowable grain agglomerations.

The non-flowable or poorly flowable powder 8 and 9 is introduced into the feed container 11 of the vibratory conveyor 1. While one would normally expect relatively coarse grains to be divided into finer grains as a result of the mechanical vibrations of the feed container 11, in this case exactly the opposite occurs. As a result of the vibrations of the feed container 11 in the direction indicated by the arrows 111, the fine grains of the powder 8 and 9 are agglomerated to form flowable, regular grain agglomerations 10 (FIG. 2c). Agglomeration occurs without the addition of lubricants such as liquids etc. The grain Agglomerations 10 (pellets) so formed flow up the feed container 11, which is wound in the manner of a spiral staircase, and over the conveyor portion 13 of that container 11 into the first filling funnel 2. The vibratory conveyor 1 therefore also acts as the conveyor means that feed the powder in the form of pellets 10 to the metering means. The density of the relatively uniform stream of grain agglomerations flowing into the filling funnel 2 is dependent upon the amplitude of the mechanical vibrations of the feed container 11: the greater the amplitude of the vibrations, the greater the density of the stream of grain agglomerations flowing into the filling funnel 2. The filling funnel 2 then feeds the pellets directly to the metering means.

The metering means comprise two plates 3 and 4 which are movable relative to each other and each have two through-openings 31 and 32 and 41 and 42, respectively, and also automatic means A for moving the movable upper plate 3. The automatic means A move the plate 3 to and fro at regular intervals between two relative positions in each of which the plate 3 stops. In the first relative position, which is shown here, one opening 32 in the movable upper plate 3 is closed at the bottom by the fixed lower plate 4 and thus forms a metering chamber. At the same time, the opening 32 is aligned with the outlet opening 21 of the first filling funnel 2, so that the metering chamber 32 can be filled with pellets 10 from above. In this first relative position of the two plates 3 and 4, the other opening 31 in the movable upper plate 3 is aligned with the opening 41 in the fixed lower plate 4 and is therefore open at the bottom. After the above-mentioned time interval has elapsed, the automatic means A move the upper plate 3 into the second relative position. The interval between the to and fro movements of the upper plate 3 is such that a quantity of pellets equal to the quantity introduced into the metering chamber 32 during that interval has in the meantime been fed via the conveyor portion 13 of the vibratory conveyor 1 to the first filling funnel 2. The pellets in the metering chamber 32 are moved together with the metering chamber 32 into the second relative position, without being crushed or squashed. In the second relative position, the opening 32 in the upper plate 3 is aligned with the opening 42 in the lower plate 4. As a result, the metering chamber 32 is open and the pellets are able to pass through the opening 42 in the lower plate to the filling means. In the second relative position, the other opening 31 in the upper plate 3 is closed at the bottom by the lower plate 4 and thus forms a metering chamber. At the same time, it is aligned at the top with the outlet opening 21 of the first filling funnel 2 so that, in the second relative position, while the metering chamber 32 is being emptied through the opening 42 in the lower plate 4, the metering chamber 31 is being filled with pellets. The lower plate 4 with its two openings 41 and 42 thus acts as an outlet valve. In each of the two relative positions, it closes whichever of the metering chambers 31 and 32 is being filled from above. At the same time, the other metering chamber 32 or 31 is opened by the corresponding opening 42 or 41 in the lower plate and the metered quantity of pellets is able to pass through that opening 42 or 41 to the filling means.

The filling means comprise a second filling funnel 5 which ends in a pipe 6. The second filling funnel 5 is structurally joined to the fixed lower plate 4 and so arranged that it collects the powder passing through the opening 41 or 42 in the lower plate 4. The powder collected by the filling funnel 5 is fed by the latter into the pipe 6 which feeds that quantity of powder to a collecting vessel 7 provided for that purpose.

An especially suitable vibratory conveyor 1 for the above-described apparatus is a helical vibrator of the WV 150 type manufactured by AFAG. However, an apparatus having a vibration device of a construction different from that of the vibratory conveyor 1 described herein is, of course, also suitable. In addition, the conveyor means 13, which transport the pellets 10 to the metering means, do not have to be part of the vibratory conveyor 1; they may also be constructed as an independent unit. It is simply necessary to ensure that the pellets are not crushed again as a result of being transported.

The metering chamber 32 does not necessarily have to be completely full when the automatic means A move the first plate 3 into the second relative position in which the metering chamber 32 is emptied as a result of the opening 32 in the first plate 3 being aligned with the opening 42 in the second plate 4. It is simply necessary to ensure that the same quantity of pellets is always discharged from the metering chamber 32 (the same naturally applies to the metering chamber 31). If the metering chamber 32 is not completely full, it may be necessary to provide level indicators which, when the quantity of pellets 10 to be metered is reached, give a signal to the automatic means A so that the plate 3 is moved into the other relative position. Although this involves greater expenditure, it has the advantage over known apparatuses and methods that, on account of the regular supply of pellets 10 to the metering chambers 31 and 32 and because of the small diameter of the pellets 10, accurate metering even of very small quantities of powder is possible.

Furthermore, in principle only one opening is required in each of the plates 3 and 4 to ensure functioning of the apparatus. For example, the opening 31 in the first plate 3 and the opening 41 in the second plate 4 may be omitted. The important factor is that the time interval between the movements of the first plate 3 into the other relative position should be such that, in the time interval in which the metering chamber 32 is emptied through the opening 42 in the second plate 4, the same quantity of pellets 10 is fed to the filling funnel 2 as was removed on emptying the metering chamber 32. It is also possible to provide a control device which, on the basis of the density of the stream of pellets 10 flowing into the metering chamber 32 or 31, controls the automatic means A in such a manner that that condition is fulfilled.

Moreover, it is not necessary for the second filling funnel 5 and the pipe 6 to be structurally joined to each other. They may each be constructed as an independent unit. Especially practical is an apparatus in which the first filling funnel 2, the two plates 3 and 4, the automatic means A, the second filling funnel 5 and the pipe 6, that is to say the metering means and the filling means, are combined to form a structural unit.

The collecting vessel 7 for the powder transported by the pipe 6 may be, for example, a conventional pharmaceutical capsule or a blister pack customarily used in the pharmaceutical industry. Naturally, storage bottles customary in the pharmaceutical industry are also suitable as such a collecting vessel.

Figure 2A:
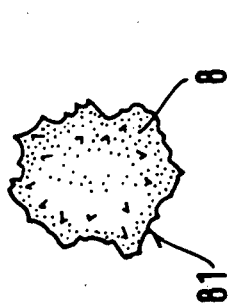
Figure 2B:
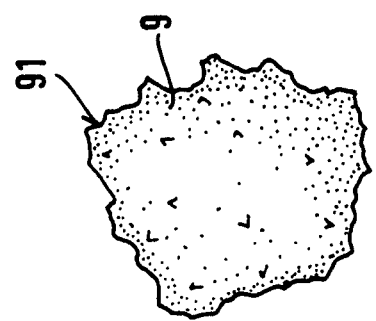

The method and the apparatus according to the invention are especially suitable for the metering of very small quantities of a poorly flowable powder mixture consisting of previously ground and/or sifted lactose and formoterol, in the present case in the form of the salt formoterol fumarate which is designated "($\pm$)-2'-hydroxy-5'-[(RS)-1-hydroxy-2-[[(RS)-p-methoxy-$\alpha$-methylphenethyl]-amino]ethyl]formanilide fumarate dihydrate" in accordance with IUPAC nomenclature. Formoterol is an active ingredient which is used for treating diseases of the human lungs or of the respiratory system, for example asthmatic diseases. The active ingredient is mixed with lactose to form a powder mixture, and the powder mixture is inhaled. The mixing ratio of formoterol to the total mixture (formoterol+lactose) is within the range of from 1:10 to 1:500. The average grain size of the formoterol is approximately 5 $\mu$m, and the average grain size of the lactose is less than 50 $\mu$m, preferably from 1 $\mu$m to 10 $\mu$m. FIGS. 2$a$–$c$ show, on a greatly enlarged scale, such formoterol grains 8 (FIG. 2$a$) and lactose grains 9 (FIG. 2$b$), the surfaces 81 and 91, respectively, of which are jagged and angular, which is one of the main causes of the poor flowability of the powder in the non-agglomerated state. By contrast, the surface 101 of the pellet 10 (FIG. 2$c$) formed by the vibrations of the vibratory conveyor 1 is substantially rounded, with the result that the pellets 10 are better able to flow. The average diameter of the pellets 10 is within the range of approximately from 50

μm to 2000 μm, depending on the average grain size of the lactose used, which is sifted prior to agglomeration. The larger the average diameter of the lactose grains 9, the softer and more unstable the agglomerations. Especially stable flowable pellets 10 are obtained when formoterol 8 having an average diameter of 5 μm and lactose having an average diameter of 10 μm are used, the mixing ratio of formoterol to the total mixture (formoterol+lactose) being approximately 1:40. The frequency of the vibrations that enable the regular pellets to be formed is preferably in the region of 100 Hz. Of course, other vibration frequencies are also possible.

As already mentioned above, the method and the apparatus according to the invention are suitable for the accurate metering of very small quantities of non-flowable or poorly flowable powders. One field of application for which the method and the apparatus are especially suitable is the accurate metering of pharmaceutical powders, especially of a mixture of formoterol and lactose, where only very small relative weight fluctuations are permissible and no lubricants (for example liquids) may be added for the formation of agglomerations.

What is claimed is:

1. A method for metering small quantities of a non-flowable or poorly flowable fine-grained powder which comprises the steps of (1) feeding said fine-grained powder to a mechanical vibration device, (2) mechanically vibrating said powder in said mechanical/vibration device to form flowable grain agglomerations, (3) transporting said agglomerations to a metering device, (4) metering the desired amounts of agglomerations and (5) collecting said metered amounts.

2. The method of claim 1, wherein said mechanical vibration device is a vibratory conveyor.

3. A method according to claim 1, wherein said non-flowable or poorly flowable powder is a mixture of formoterol and lactose.

4. A method according to claim 3, wherein said mixture is used in a mixing ratio of formoterol to the total mixture of from 1:10 to 1:500.

5. A method according to claim 3, wherein said formoterol has an average grain size of approximately 5 μm and said lactose has an average grain size of from 1 μm to approximately 50 μm.

6. A method according to claim 1, wherein grain agglomerations having an average diameter of approximately from 50 μm to 2000 μm are formed.

* * * * *